(12) United States Patent
Humphreys

(10) Patent No.: US 8,562,656 B2
(45) Date of Patent: Oct. 22, 2013

(54) RETAINING MECHANISM

(75) Inventor: Kevin R. Humphreys, Memphis, TN (US)

(73) Assignee: Warsaw Orrthopedic, Inc., Warsaw, IN (US)

( * ) Notice: Subject to any disclaimer, the term of this patent is extended or adjusted under 35 U.S.C. 154(b) by 286 days.

(21) Appl. No.: 12/905,856

(22) Filed: Oct. 15, 2010

(65) Prior Publication Data

US 2012/0095513 A1    Apr. 19, 2012

(51) Int. Cl.
*A61B 17/80* (2006.01)

(52) U.S. Cl.
USPC ........................................... 606/289

(58) Field of Classification Search
USPC .................. 606/286–290; 411/533
See application file for complete search history.

(56) References Cited

U.S. PATENT DOCUMENTS

| | | |
|---|---|---|
| 5,085,548 A | 2/1992 | Moyles |
| 5,098,435 A | 3/1992 | Stednitz et al. |
| 5,261,910 A | 11/1993 | Warden et al. |
| 5,290,312 A | 3/1994 | Kojimoto et al. |
| 5,318,567 A | 6/1994 | Vichard |
| 5,364,399 A | 11/1994 | Lowery et al. |
| 5,470,333 A | 11/1995 | Ray |
| 5,484,439 A | 1/1996 | Olson et al. |
| 5,484,440 A | 1/1996 | Allard |
| 5,520,690 A | 5/1996 | Erico et al. |
| 5,531,746 A | 7/1996 | Errico et al. |
| 5,549,607 A | 8/1996 | Olson et al. |
| 5,549,612 A | 8/1996 | Yappe et al. |
| 5,562,661 A | 10/1996 | Yoshimi et al. |
| 5,578,034 A | 11/1996 | Estes |
| 5,607,426 A | 3/1997 | Ralph et al. |
| 5,611,800 A | 3/1997 | Davis et al. |
| 5,616,144 A | 4/1997 | Yapp et al. |
| 5,634,925 A | 6/1997 | Urbanski |
| 5,676,666 A | 10/1997 | Oxland et al. |
| 5,681,311 A | 10/1997 | Foley et al. |
| 5,713,900 A | 2/1998 | Benzel et al. |
| 5,728,098 A | 3/1998 | Sherman et al. |
| 5,735,853 A | 4/1998 | Olerud |
| 5,735,899 A | 4/1998 | Schwartz et al. |
| 5,766,254 A | 6/1998 | Gelbard |
| 5,800,433 A | 9/1998 | Benzel et al. |
| 5,843,082 A | 12/1998 | Yuan et al. |
| 5,876,402 A | 3/1999 | Errico et al. |

(Continued)

FOREIGN PATENT DOCUMENTS

| | | |
|---|---|---|
| EP | 1169971 | 9/2002 |
| EP | 1346697 | 9/2003 |
| FR | 2794963 | 12/2000 |
| WO | 9535067 | 12/1995 |

*Primary Examiner* — Anu Ramana

(57) ABSTRACT

A retaining mechanism for use in affixing a stratum to bone is disclosed. The retaining mechanism comprises a stratum, a shoulder element and a retaining element. The stratum comprises a first surface, a second surface, and at least one hole extending between the first surface and the second surface, wherein the second surface is configured to engage at least a portion of the bone. The shoulder element is configured to engage the stratum and configured to at least partially overlap the at least one hole. The retaining element is configured to engage the stratum and configured to at least partially overlap the shoulder element such that the shoulder element helps prevent inadvertent backing out of a fastener after the fastener has been fully inserted into the at least one hole.

18 Claims, 18 Drawing Sheets

(56) References Cited

U.S. PATENT DOCUMENTS

| | | |
|---|---|---|
| 5,904,683 A | 5/1999 | Pohndorf et al. |
| 5,931,838 A | 8/1999 | Vito |
| 5,954,722 A | 9/1999 | Bono |
| 5,954,725 A | 9/1999 | Shermann et al. |
| 6,004,321 A | 12/1999 | Graser |
| 6,017,345 A | 1/2000 | Richelsoph |
| 6,030,389 A | 2/2000 | Wagner et al. |
| 6,036,693 A | 3/2000 | Yuan et al. |
| 6,077,267 A | 6/2000 | Huene |
| 6,117,135 A | 9/2000 | Schlapfer |
| 6,117,713 A | 9/2000 | Hoshino et al. |
| 6,132,434 A | 10/2000 | Shermann et al. |
| 6,152,927 A | 11/2000 | Farris et al. |
| 6,159,213 A | 12/2000 | Rogozinski |
| 6,189,422 B1 | 2/2001 | Stihl |
| 6,193,720 B1 | 2/2001 | Yuan et al. |
| 6,224,602 B1 | 5/2001 | Hayes |
| 6,228,085 B1 | 5/2001 | Theken et al. |
| 6,235,034 B1 | 5/2001 | Bray |
| 6,241,731 B1 | 6/2001 | Fiz |
| 6,258,089 B1 | 7/2001 | Campbell et al. |
| 6,261,291 B1 | 7/2001 | Talaber et al. |
| 6,273,888 B1 | 8/2001 | Justis |
| 6,273,889 B1 | 8/2001 | Richelsoph |
| 6,287,311 B1 | 9/2001 | Shermann et al. |
| 6,302,883 B1 | 10/2001 | Bono |
| 6,306,136 B1 | 10/2001 | Baccelli |
| 6,331,179 B1 | 12/2001 | Freid et al. |
| 6,342,055 B1 | 1/2002 | Eisemann et al. |
| 6,361,537 B1 | 3/2002 | Anderson |
| 6,383,186 B1 | 5/2002 | Michelson |
| 6,398,783 B1 | 6/2002 | Michelson |
| 6,402,756 B1 | 6/2002 | Ralph |
| 6,413,259 B1 | 7/2002 | Lyons |
| 6,416,528 B1 | 7/2002 | Michelson |
| 6,428,542 B1 | 8/2002 | Michelson |
| 6,440,136 B1 | 8/2002 | Gambale |
| 6,454,771 B1 | 9/2002 | Michelson |
| 6,454,773 B1 | 9/2002 | Shermann |
| 6,456,769 B1 | 9/2002 | Furusawa et al. |
| 6,485,491 B1 | 11/2002 | Farris et al. |
| 6,503,250 B2 | 1/2003 | Paul |
| 6,513,814 B2 | 2/2003 | White |
| 6,527,776 B1 | 3/2003 | Michelson |
| 6,533,786 B1 | 3/2003 | Needham et al. |
| 6,592,586 B1 | 7/2003 | Michelson |
| 6,599,290 B2 | 7/2003 | Bailey et al. |
| 6,602,255 B1 | 8/2003 | Campbell et al. |
| 6,602,256 B1 | 8/2003 | Hayes |
| 6,602,257 B1 | 8/2003 | Thramann |
| 6,605,090 B1 | 8/2003 | Trieu et al. |
| 6,620,163 B1 | 9/2003 | Michelson |
| 6,626,907 B2 | 9/2003 | Campbell et al. |
| 6,652,525 B1 | 11/2003 | Assaker et al. |
| 6,656,181 B2 | 12/2003 | Dixon et al. |
| 6,660,004 B2 | 12/2003 | Barker et al. |
| 6,666,867 B2 | 12/2003 | Ralph et al. |
| 6,669,700 B1 | 12/2003 | Farris et al. |
| 6,679,883 B2 | 1/2004 | Hawkes et al. |
| 6,682,564 B1 | 1/2004 | Duarte |
| 6,689,134 B2 | 2/2004 | Ralph et al. |
| 6,695,845 B2 | 2/2004 | Dixon et al. |
| 6,695,846 B2 | 2/2004 | Richelsoph et al. |
| 6,702,817 B2 | 3/2004 | Beger et al. |
| 6,755,833 B1 | 6/2004 | Paul et al. |
| 6,761,719 B2 | 7/2004 | Justis |
| 6,780,186 B2 | 8/2004 | Errico et al. |
| 6,793,658 B2 | 9/2004 | LeHuec et al. |
| 7,144,396 B2 * | 12/2006 | Shluzas .................. 606/266 |
| 2002/0013586 A1 | 1/2002 | Justis |
| 2002/0045897 A1 | 4/2002 | Dixon et al. |
| 2002/0045898 A1 | 4/2002 | Freid |
| 2002/0058939 A1 | 5/2002 | Wagner et al. |
| 2009/0012571 A1 * | 1/2009 | Perrow et al. ............ 606/280 |

\* cited by examiner

RETAINING MECHANISM

FIELD OF INVENTION

The present invention is directed to systems for affixing a stratum to bone.

BACKGROUND

The present disclosure relates to retaining mechanisms, and more particularly, systems for affixing a stratum to bone.

SUMMARY OF THE INVENTION

A retaining mechanism for use in affixing a stratum to bone is disclosed. The retaining mechanism comprises a stratum, a shoulder element and a retaining element. The stratum comprises a first surface, a second surface, and at least one hole extending between the first surface and the second surface, wherein the second surface is configured to engage at least a portion of the bone. The shoulder element is configured to engage the stratum and configured to at least partially overlap the at least one hole. The retaining element is configured to engage the stratum and configured to at least partially overlap the shoulder element such that the shoulder element helps prevent inadvertent backing out of a fastener after the fastener has been fully inserted into the at least one hole.

Further, methods of implanting a spinal plate using the retaining mechanism are disclosed.

DETAILED DESCRIPTION

Figure 1:
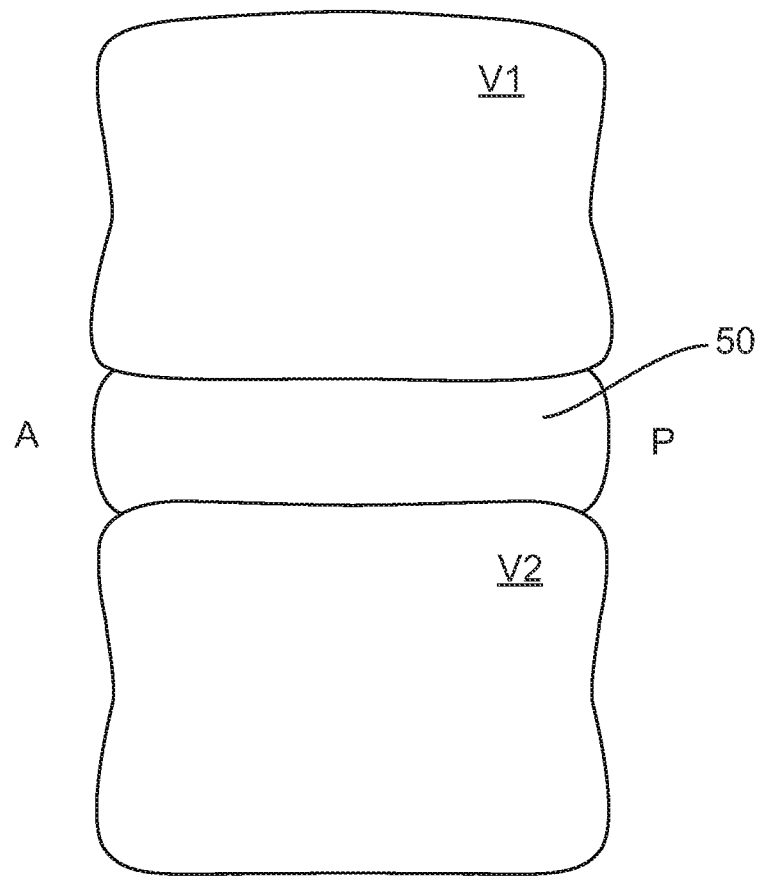
FIG. 1 is a schematic, cross-sectional view of two adjacent vertebral bodies.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 shows a schematic, cross-sectional view of two adjacent vertebral bodies V1 and V2 with an intervertebral disc 50 situated in its natural location between the two vertebral bodies V1 and V2. As shown in FIG. 1, vertebral body V1 represents a superior vertebral body and V2 represents an inferior vertebral body. Reference marker A represents an anterior side of the vertebral bodies V1 and V2, whereas reference marker P represents a posterior side of the vertebral bodies V1 and V2.

Figure 2:
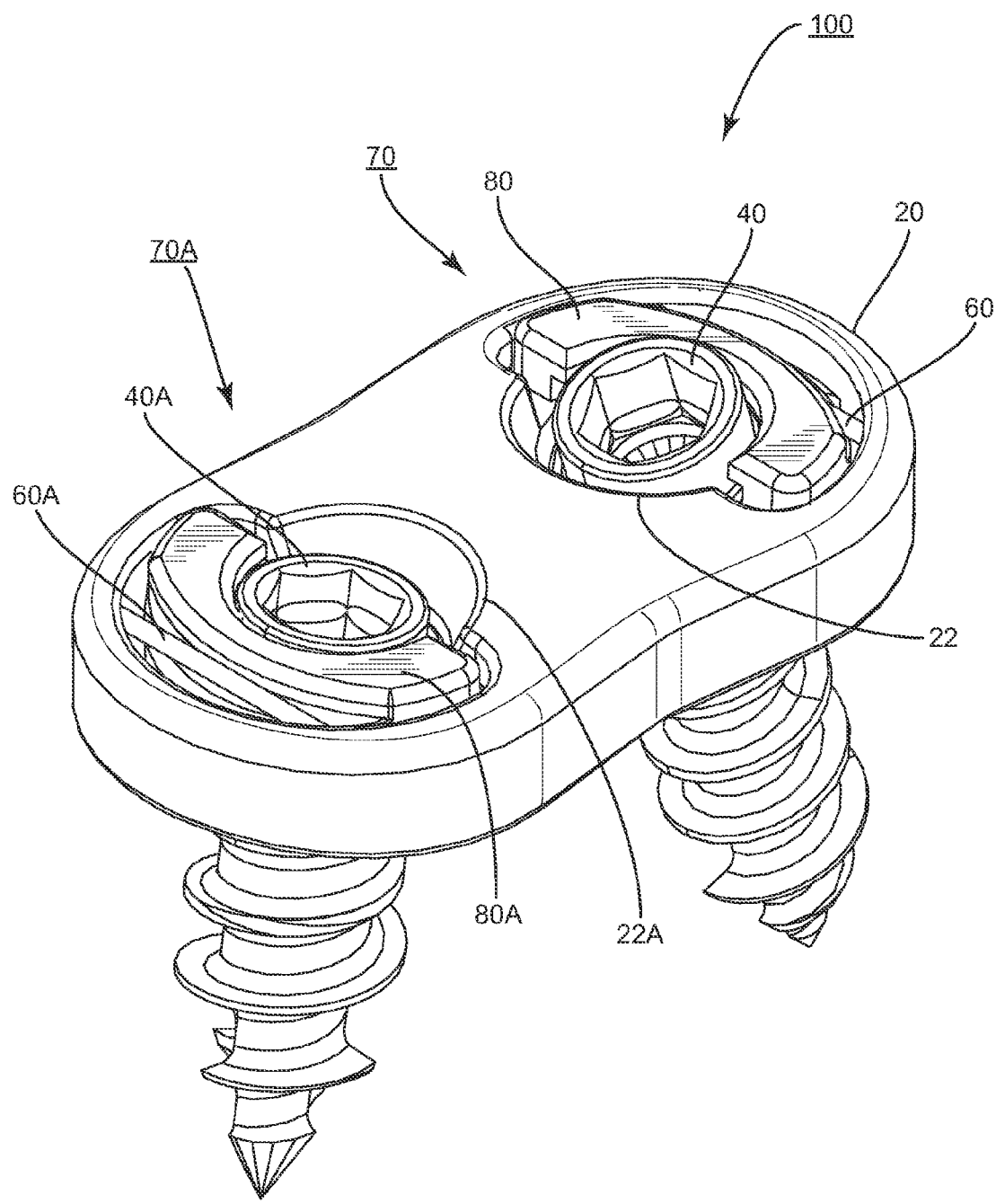
FIG. 2 is an isometric view of a system for affixing a stratum to bone.

FIG. 2 shows an isometric view of a system 100 for affixing a stratum 20 to bone, for example, V1 and/or V2. The system 100 comprises a retaining mechanism 70 that comprises a stratum 20, a shoulder element 80 and a retaining element 60. Further, as shown in FIG. 2, the stratum 20 comprises at least one hole 22 and the system 100 further comprises a fastener 40, which is shown inserted in hole 22. In addition, as shown in FIG. 2, the system 100 further comprises a second retaining mechanism 70A that comprises the stratum 20, a second shoulder element 80A and a second retaining element 60A. Further, as shown in FIG. 2, the stratum 20 further comprises a second hole 22A and the system 100 further comprises a second fastener 40A. Note that in the context of spinal plates, other embodiments may, for example, utilize a stratum having a length longer than that shown in FIG. 2 so as to accommodate three or more holes for joining two or more levels, i.e, for connecting three or more adjacent vertebral bodies.

Figure 3:
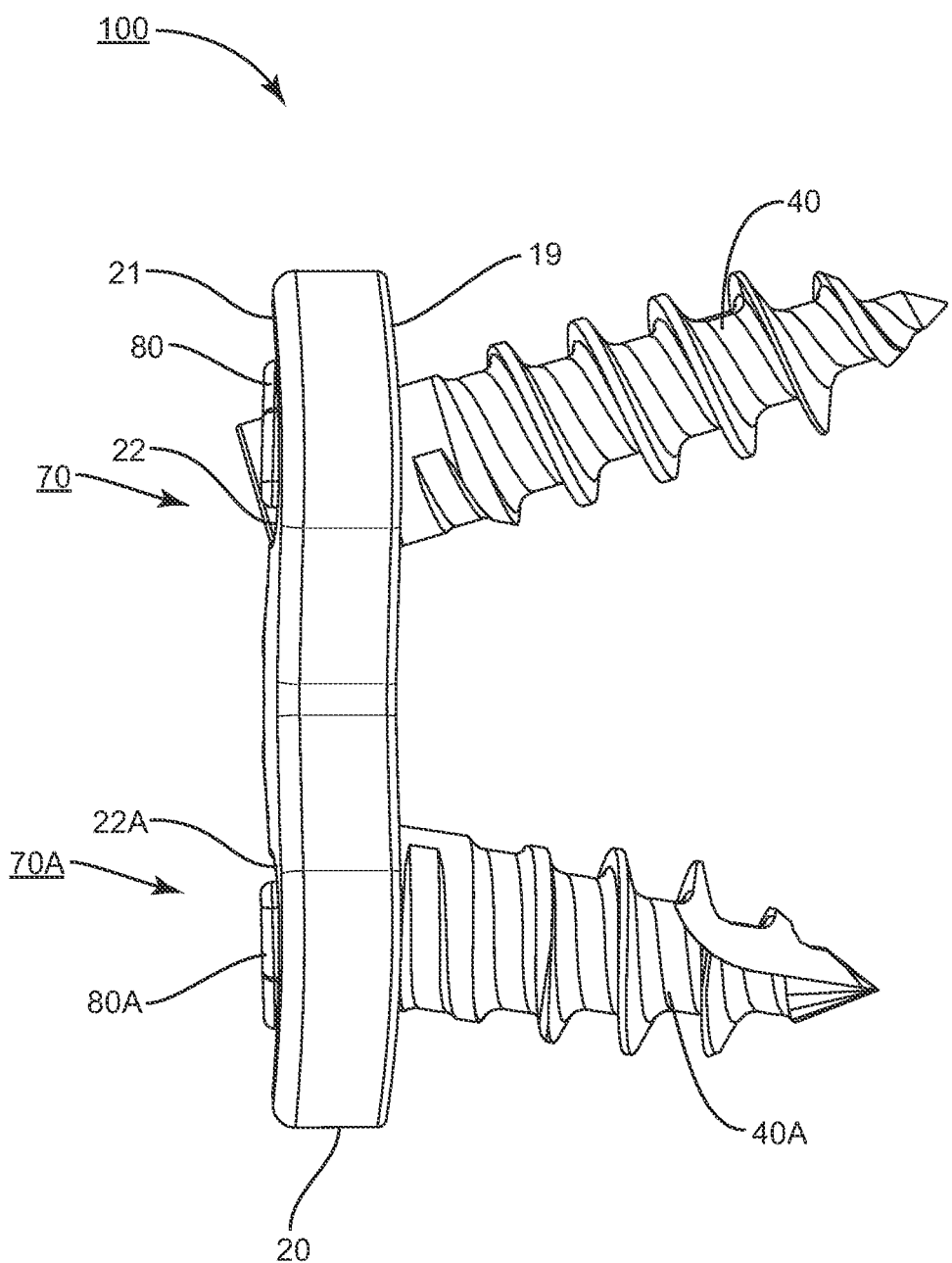
FIG. 3 is a side view of the system of FIG. 2.

FIG. 3 shows a side view of system 100. As shown, the stratum 20 comprises a first surface 21, a second surface 19, and at least one hole 22 or 22A extending between the first surface 21 and the second surface 19, wherein the second surface 19 is configured to engage at least a portion of the bone, for example, V1 and/or V2. As shown in FIG. 3, system 100 comprises the first retaining mechanism 70 and the second retaining mechanism 70A.

Figure 4:
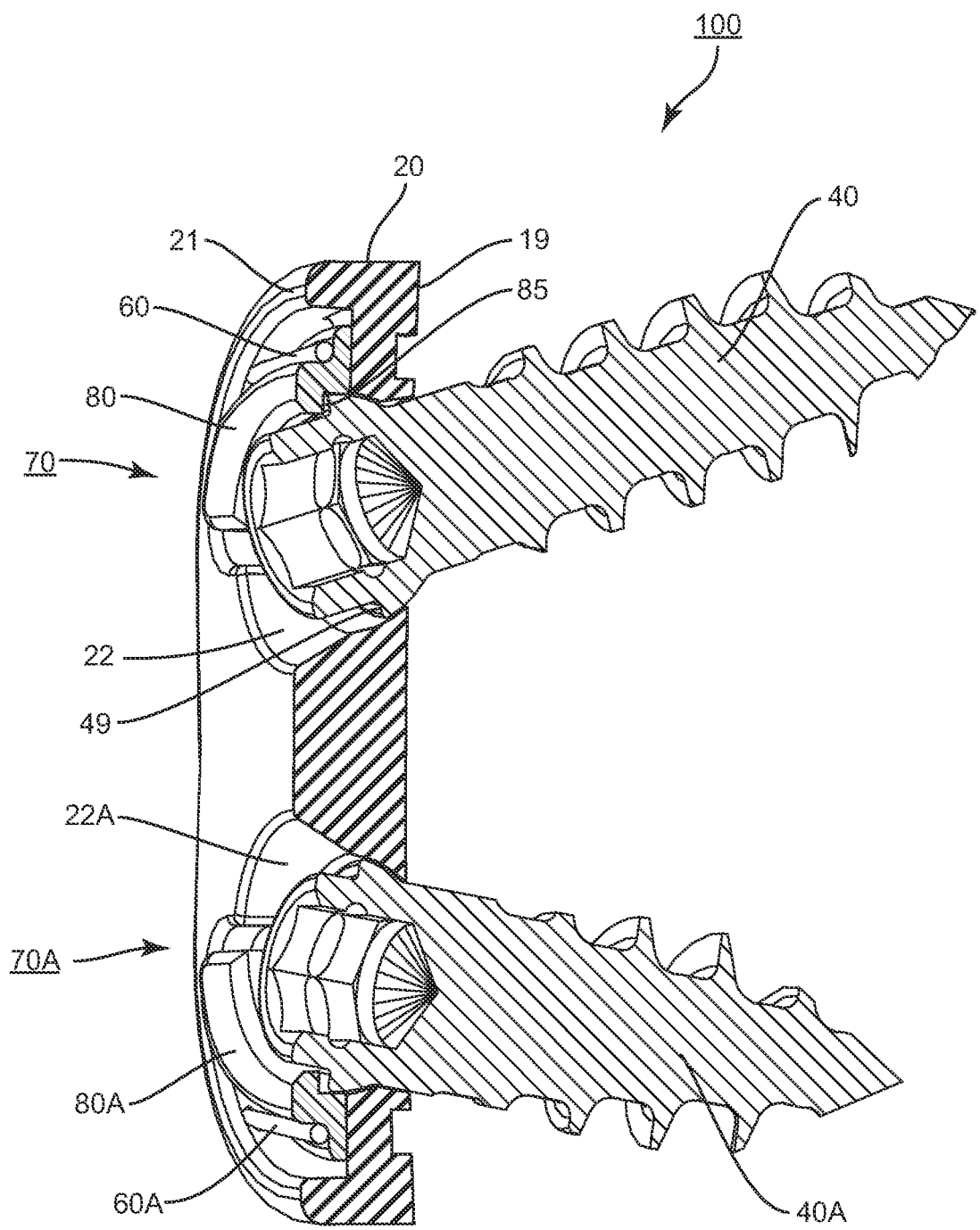
FIG. 4 is a cross-sectional, isometric view of the system of FIG. 2.

FIG. 4 shows a cross-sectional, isometric view of the system 100. As shown, retaining mechanism 70 comprises the stratum 20, the shoulder element 80 and the retaining element 60. The shoulder element 80 is configured to engage the stratum 20 and configured to at least partially overlap the at least one hole 22. The retaining element 60 is configured to engage the stratum 20 and configured to at least partially overlap the shoulder element 80 such that the shoulder element 80 helps prevent inadvertent backing out of the fastener 40 after the fastener 40 has been fully inserted into the at least one hole 22. Further, as shown in FIG. 4, retaining mechanism 70A comprises the stratum 20, the shoulder element 80A and the retaining element 60A. The shoulder element 80A is configured to engage the stratum 20 and configured to at least partially overlap the at least one hole 22A. The retaining element 60A is configured to engage the stratum 20 and configured to at least partially overlap the shoulder element 80A such that the shoulder element 80A helps prevent inadvertent backing out of the fastener 40A after the fastener 40A has been fully inserted into the at least one hole 22A. Further, note that not only is the retaining element 60 or 60A configured to engage stratum 20, but the stratum 20 is configured to engage the retaining element 60 or 60A. Similarly, not only is the shoulder element 80 or 80A configured to engage stratum 20, but the stratum 20 is configured to engage the shoulder element 80 or 80A.

Figure 5:
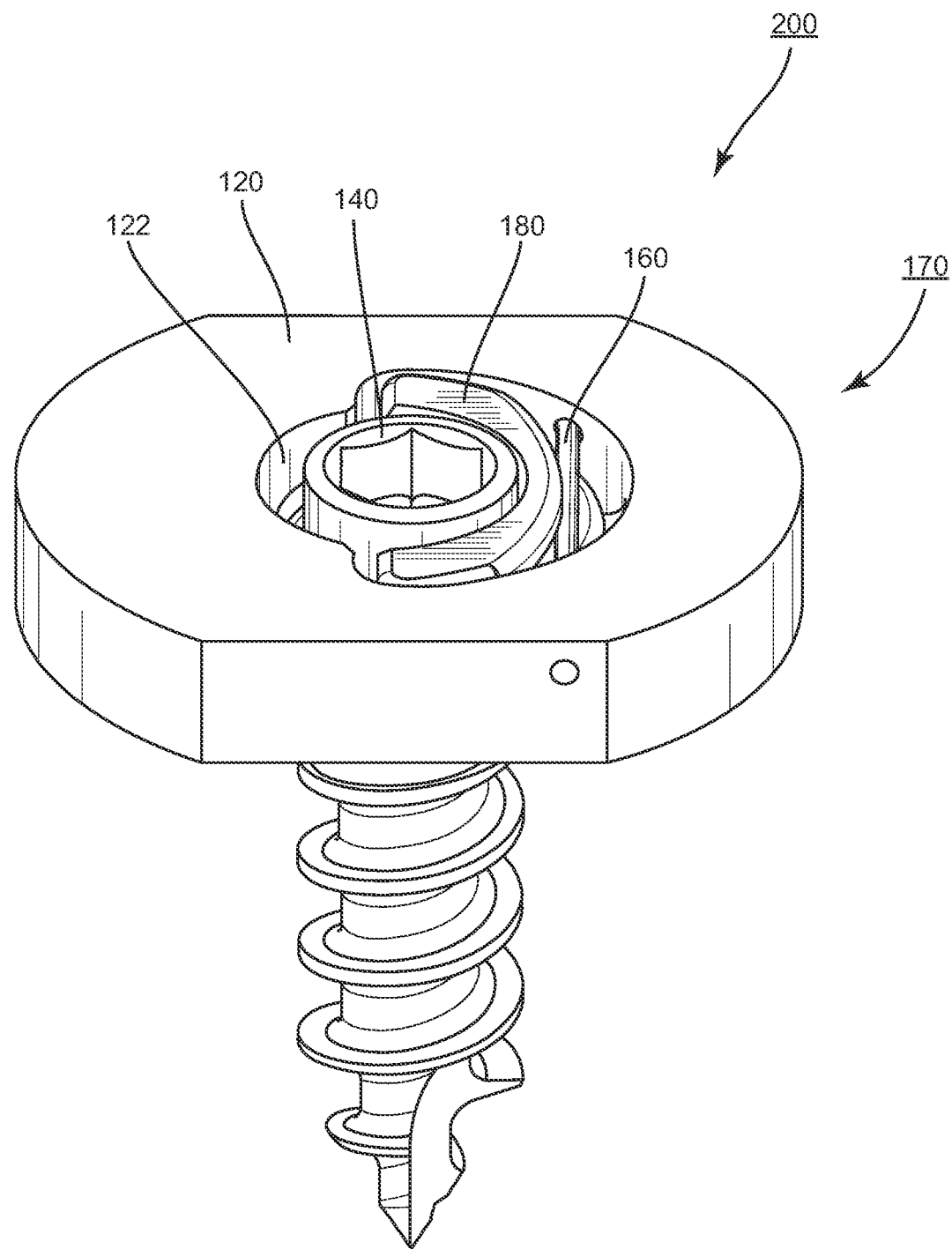
FIG. 5 shows an isometric view of a system used to help illustrate the workings of the system of FIG. 2.

FIG. 5 shows an isometric view of a system 200 used to help illustrate how the aforementioned retaining mechanisms and systems work. Specifically, for illustrative purposes only, FIG. 5 and the remaining figures show a stratum 120 having only one hole 122. FIG. 5 shows a system 200 that comprises a retaining mechanism 170 that comprises a stratum 120, a shoulder element 180 and a retaining element 160. Further, as shown in FIG. 5, the stratum 120 comprises one hole 122 and the system 200 further comprises a fastener 140, which is shown inserted in hole 122.

Figure 6:
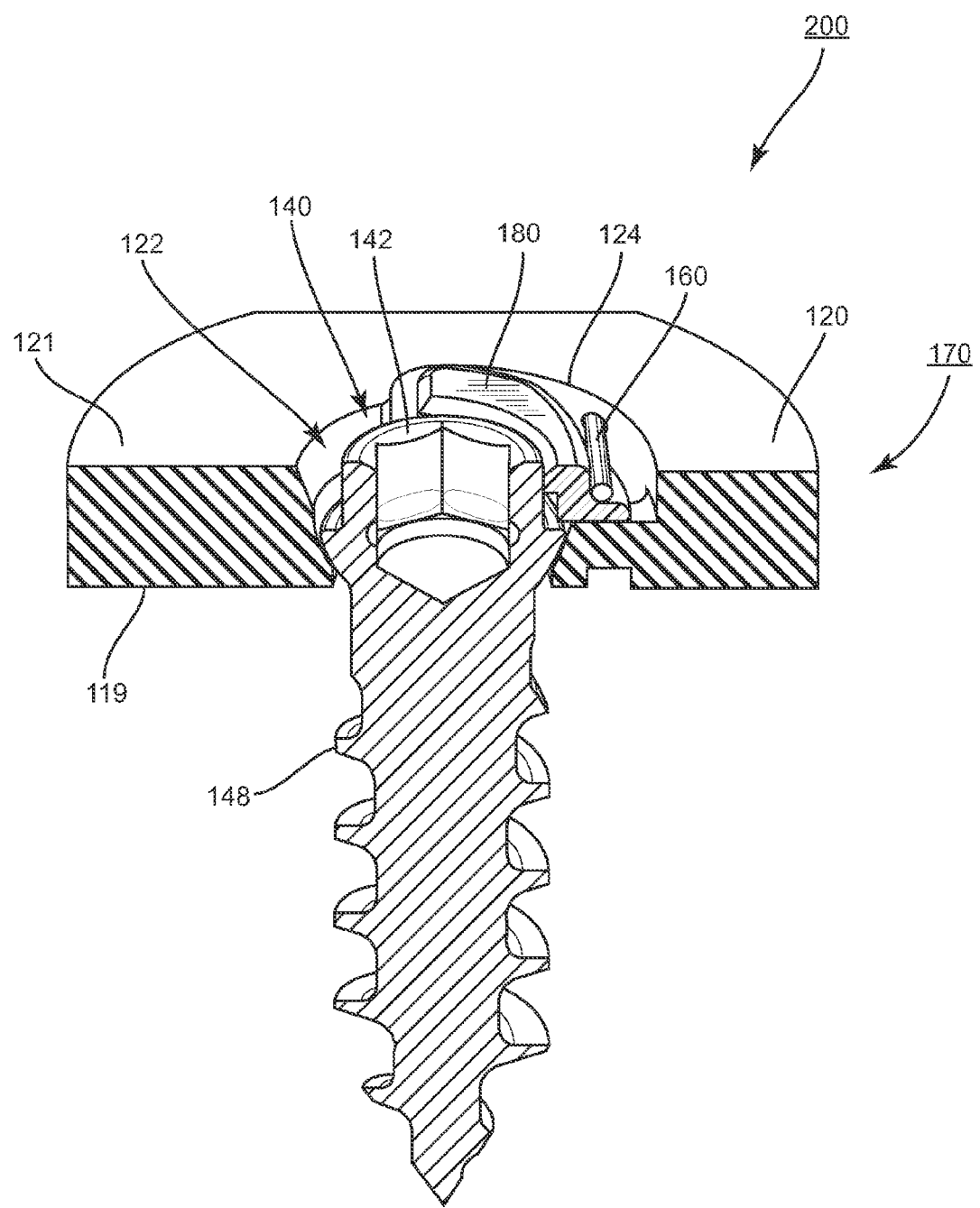
FIG. 6 is a cross-sectional, isometric view of the system of FIG. 5.

FIG. 6 shows a cross-sectional, isometric view of the system 200. As shown in FIG. 5, the stratum 120 comprises a first surface 121, a second surface 119, and at least one hole 122 extending between the first surface 121 and the second surface 119, wherein the second surface 119 is configured to engage at least a portion of the bone, for example, V1 or V2. Further, as shown in FIG. 6, retaining mechanism 170 comprises the stratum 120, the shoulder element 180 and the retaining element 160. The shoulder element 180 is configured to engage the stratum 120 and configured to at least partially overlap the at least one hole 122. The retaining element 160 is configured to engage the stratum 120 and configured to at least partially overlap the shoulder element 180 such that the shoulder element 180 helps prevent inadvertent backing out of the fastener 140 after the fastener 140 has been fully inserted into the at least one hole 122. In addition, as shown in FIG. 6, the fastener 140 comprises a head portion 142 configured for manipulation by a user and a shaft portion 148 configured to engage at least a portion of the bone.

Figure 7:
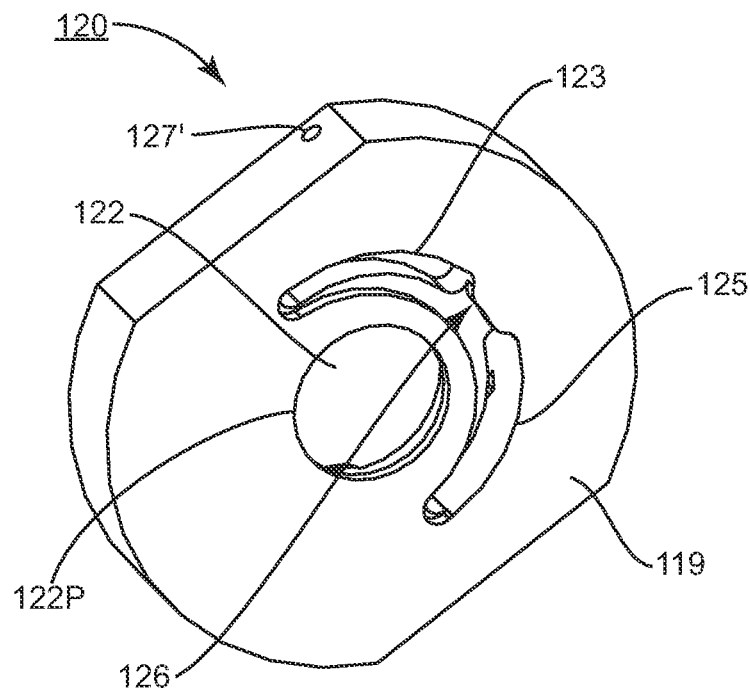
FIG. 7 is an isometric view of the bottom surface of the stratum of FIG. 5.
Figure 8:
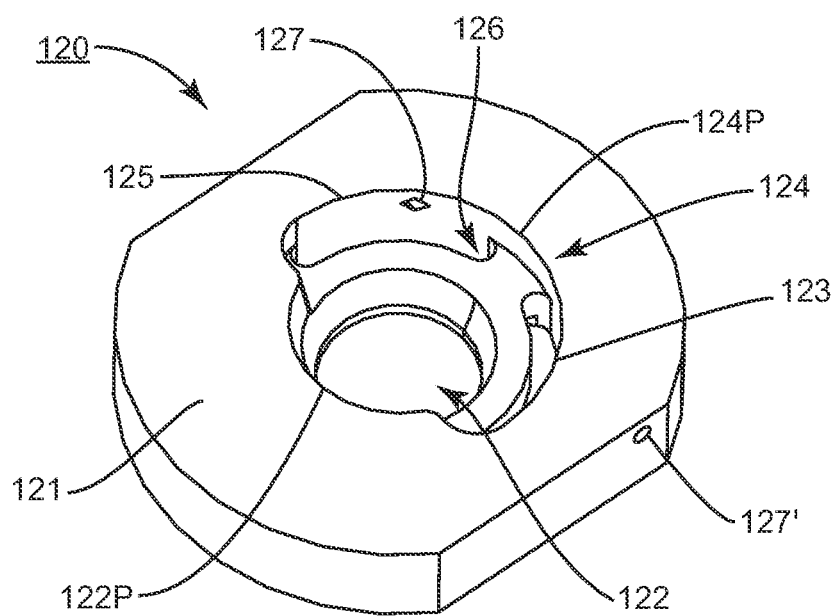
FIG. 8 is an isometric view of the top surface the stratum of FIG. 5.

FIG. 7 shows an isometric view of the bottom surface or the second surface 119 of stratum 120. As shown in FIG. 7, stratum 120 comprises hole 122, a first shoulder hole 123 and a second shoulder hole 125. The two shoulder holes 123 and 125 are situated radially outward from hole 122 and a neck portion 126 of the stratum 120 is situated between the two shoulder holes 123 and 125. FIG. 8 shows an isometric view of the top surface or the first surface 121 of stratum 120. As shown in FIG. 8, the first shoulder hole 123, the second shoulder hole 125 and the neck portion 126 situated between the two holes 123 and 125 are visible.

As shown in FIG. 7, on bottom surface 119, hole 122 has a perimeter 122P at a first radius that is constant around all 360 degrees. As shown in FIG. 8, however, on top surface 121, hole 122 has a perimeter 122P that spans less than 180 degrees. As shown in FIG. 8, stratum 120 further comprises a recess 124 that spans the remainder of the 360 degrees at surface 121. As shown, recess 124 is arcuately shaped and has a perimeter 124P situated at a second radius, wherein the second radius is greater than the first radius of perimeter 122P. In addition, as shown in FIG. 8, stratum 120 further comprises slots 127 and 127' for helping maintain the intended position of retaining element 160.

Figure 9:
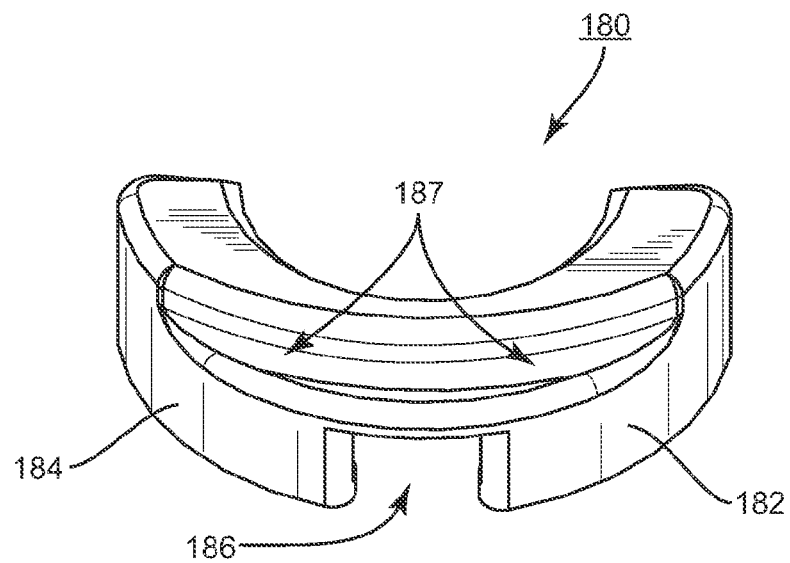
FIG. 9 is a top isometric view of the shoulder element of FIG. 5.
Figure 10:
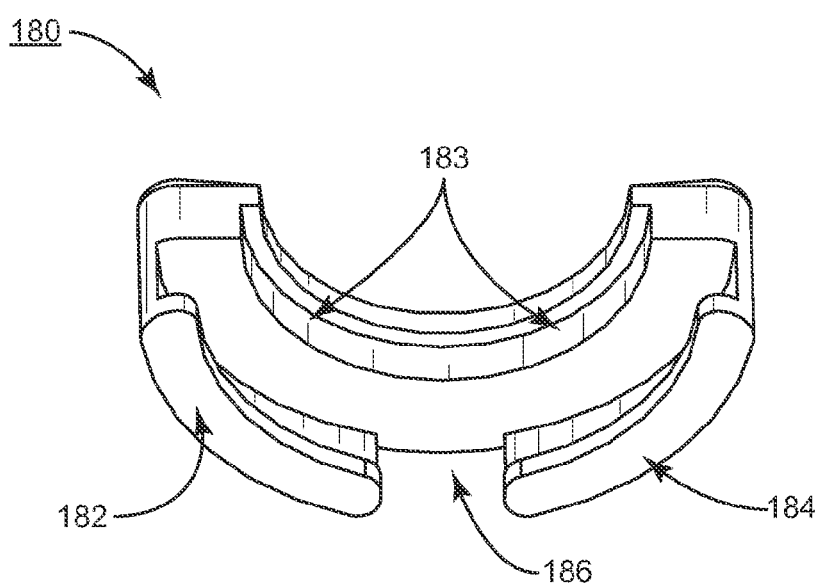
FIG. 10 is a bottom isometric view of the shoulder element of FIG. 5.

FIG. 9 shows a top isometric view of the shoulder element 180, whereas FIG. 10 shows a bottom isometric view of the shoulder element 180. As shown, shoulder element 180 comprises a first lug 182, a second lug 184 and notch 186 situated between the first and second lugs 182 and 184. Further, as shown, the first and second lugs 182 and 184 each have an arcuate shape. As shown in FIG. 9, shoulder element 180 further comprises a stop 187 for engagement with the retaining element 160. As shown in FIG. 10, shoulder element 180 further comprises groove areas 183 for engaging the fastener 140.

Figure 11:
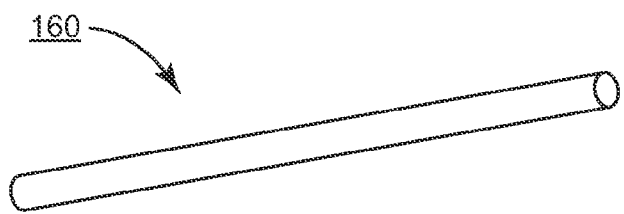
FIG. 11 is an isometric view of the retaining element of FIG. 5.

FIG. 11 shows an isometric view of the retaining element 160. As shown, retaining element 160 is rod-shaped. In the embodiments shown, the retaining element 160 comprises a material that has elastic properties. For example, retaining element 160 may comprise a material such as metal that is elastic. For example, retaining element 160 may be made of Nickel Titanium (NiTi), commercially pure Titanium or a Titanium alloy. Further, note that the retaining element 160 may have shapes other than a rod. That is, the retaining element 160 may take any form that satisfies its function described herein, for example, being able to adequately engage with the shoulder element 160 and the stratum 120 and being able to deflect enough to allow a fastener 140 to both enter the hole 122 and to sufficiently maintain position so as to not allow the fastener 140 to inadvertently back out of the stratum 120.

Figure 12:
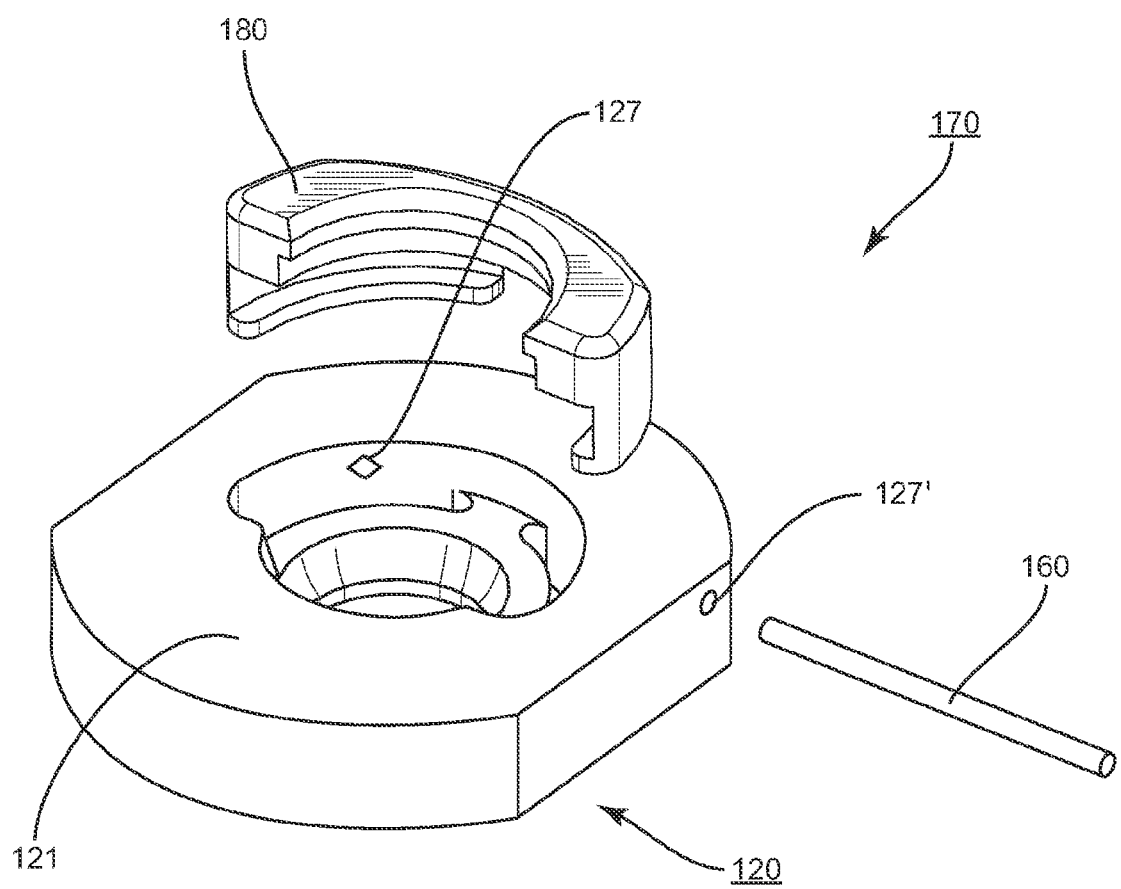
FIG. 12 is a top, exploded-isometric view of the retaining mechanism of FIG. 5.

In the embodiments described herein, the first and second shoulder holes 123 and 125 of stratum 120 accommodate and engage with the first and second lugs 184 and 182, respectively. FIG. 12 shows a top, exploded-isometric view of retaining mechanism 170. Also, FIG. 12 may be used to illustrate how the retaining mechanism 170 may be assembled. As shown, in the direction toward the stratum 120 and toward surface 121 of the stratum 120, shoulder element 180 is placed into the stratum 120 so that the first and second lugs 184 and 182 engage with the first and second shoulder holes 123 and 125 of stratum 120. Thereafter, the retaining element 160 may be inserted into the stratum 120. For example, retaining element 160 may be inserted through slot 127' until it is situated on or adjacent stop 187 and maintained in place with slots 127 and 127'. Note that the retaining element 160 need not be inserted through the side of the stratum, but may, for example, be merely placed in position from the direction toward surface 121 and lodged in place on or adjacent stop 187. Further, something other than slots 127 and 127' may be used to maintain the retaining element 160 is position as long as its function is accomplished.

Figure 13:
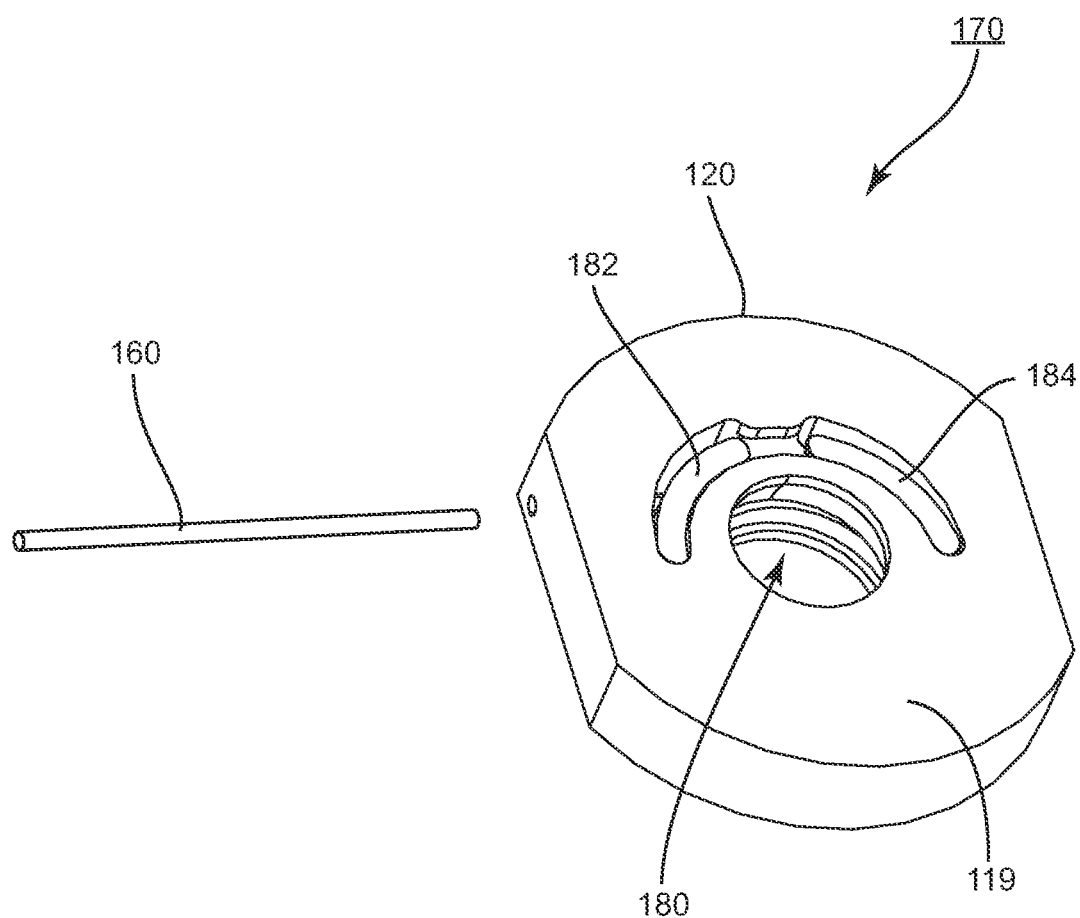
FIG. 13 is a bottom, isometric view of the retaining mechanism of FIG. 5.

FIG. 13 shows a bottom, isometric view of retaining mechanism 170. As shown in FIG. 13, the shoulder element 180 has been placed into the stratum 120 and the first and second lugs 184 and 182 are shown engaged with the first and second shoulder holes 123 and 125 of stratum 120. As shown, the retaining element 160 has not yet been inserted into the stratum 120.

Further, note that although the shoulder element 180 is shown as having an arcuate shape, it may have different shapes, for example a more straight length of material or that having a more rectangular shape. That is, the shoulder element 180 may take any form that satisfies its function described herein, for example, being able to adequately engage with the stratum 120, at least partially overlap the at least one hole 122 and being substantially rigid so that when the fastener 140 is in its fully-inserted position and the retaining member 160 at least partially overlaps the shoulder element 180, that the shoulder element 180 helps prevent inadvertently backing out of the fastener 140.

Figure 14:
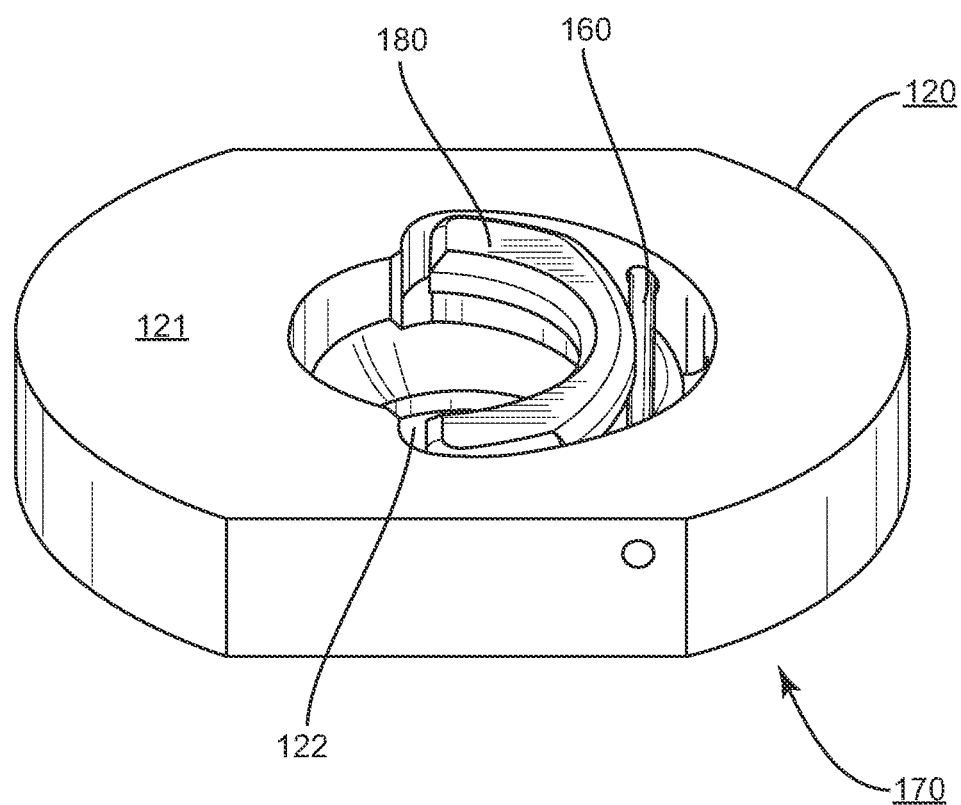
FIG. 14 is a top, isometric view of the retaining mechanism of FIG. 5.

FIG. 14 shows a top, isometric view of retaining mechanism 170. As shown in FIG. 14, the shoulder element 180 and the retaining element 160 have both been placed into the stratum 120. As shown in FIG. 14, the shoulder element 180 is in its second position that at least partially overlaps the at least one hole 122. When a fastener such as fastener 140 is in its fully-inserted position, the shoulder element 180 is in its second position. Unless moved out of the second position, however, the shoulder element 180 tends to remain in the second position. Thus, as shown in FIG. 14, before a fastener such as fastener 140 is inserted into the hole 122, the shoulder element 180 may be in the second position.

Figure 15:
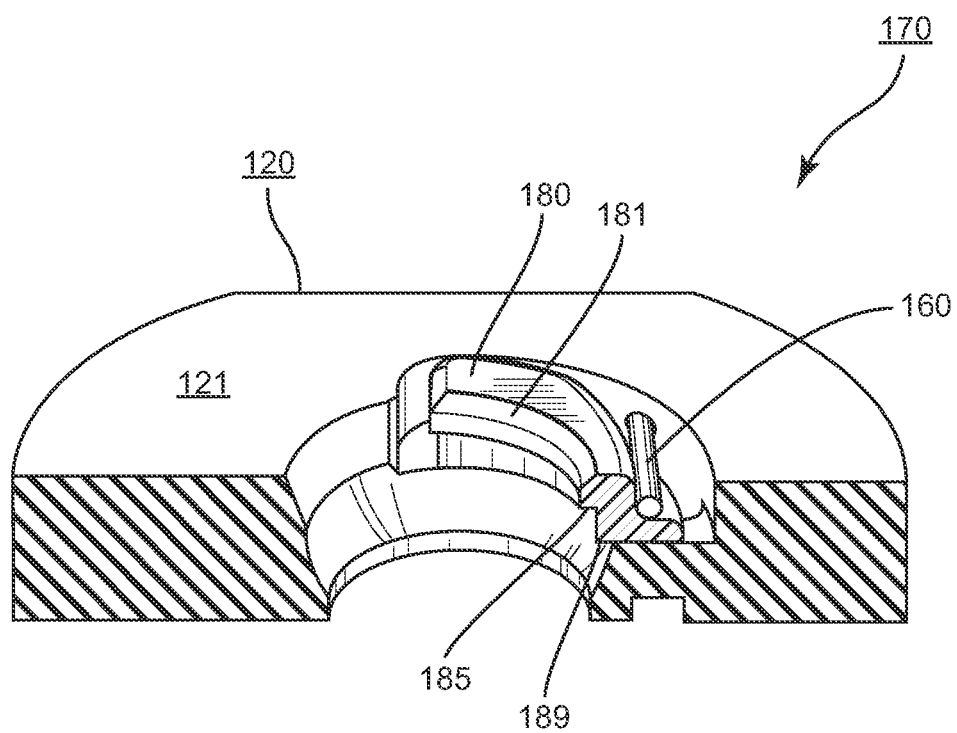
FIG. 15 is a cross-sectional, top-isometric view of the retaining mechanism of FIG. 5.

FIG. 15 shows a cross-sectional, top-isometric view of retaining mechanism 170 of FIG. 14. As shown in FIG. 15, the shoulder element 180 and the retaining element 160 have both been placed into the stratum 120. Also, as shown in FIG. 14, the shoulder element 180 is in its second position that at least partially overlaps the at least one hole 122. In addition, as shown in FIG. 15, the shoulder element 180 comprises a lip 181, a first underside surface 185 and a second underside surface 189.

Figure 16:
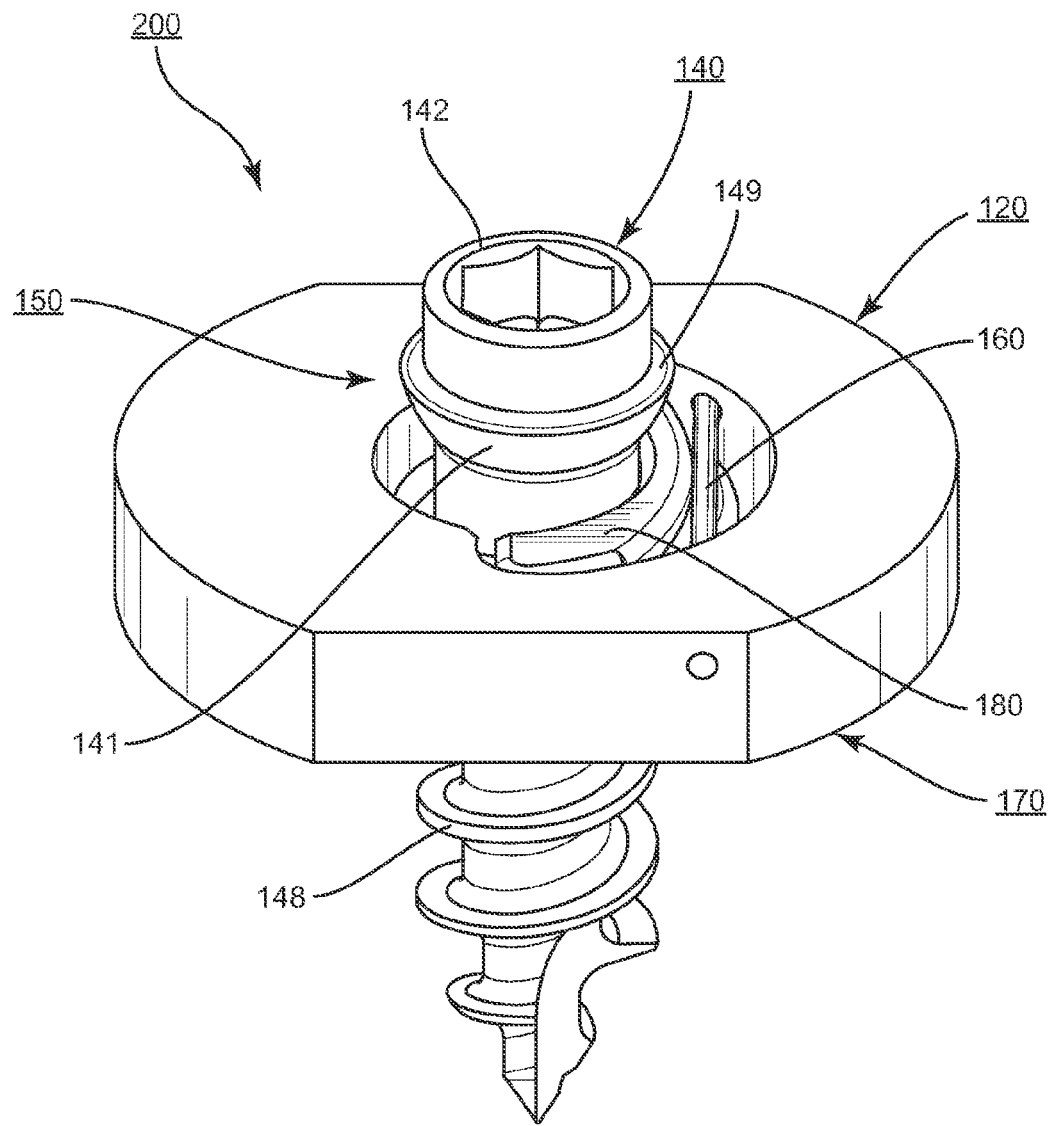
FIG. 16 is a top, isometric view of the system of FIG. 5.

FIG. 16 shows a top, isometric view of system 200 which comprises retaining mechanism 170 and a fastener 140. As shown in FIG. 16, the shoulder element 180 and the retaining element 160 have both been placed into the stratum 120, but as compared to that shown in FIG. 14, the fastener 140 has been partially inserted into the hole 122, but not fully-inserted into the hole 122. In addition, as shown in FIG. 16, the fastener 140 comprises a head portion 142 and a shaft portion 148. Further, as shown in FIG. 16, the head portion 142 of the fastener 140 comprises a ledge 150 that comprises an upper surface 149 and an underside surface 141.

Figure 17:
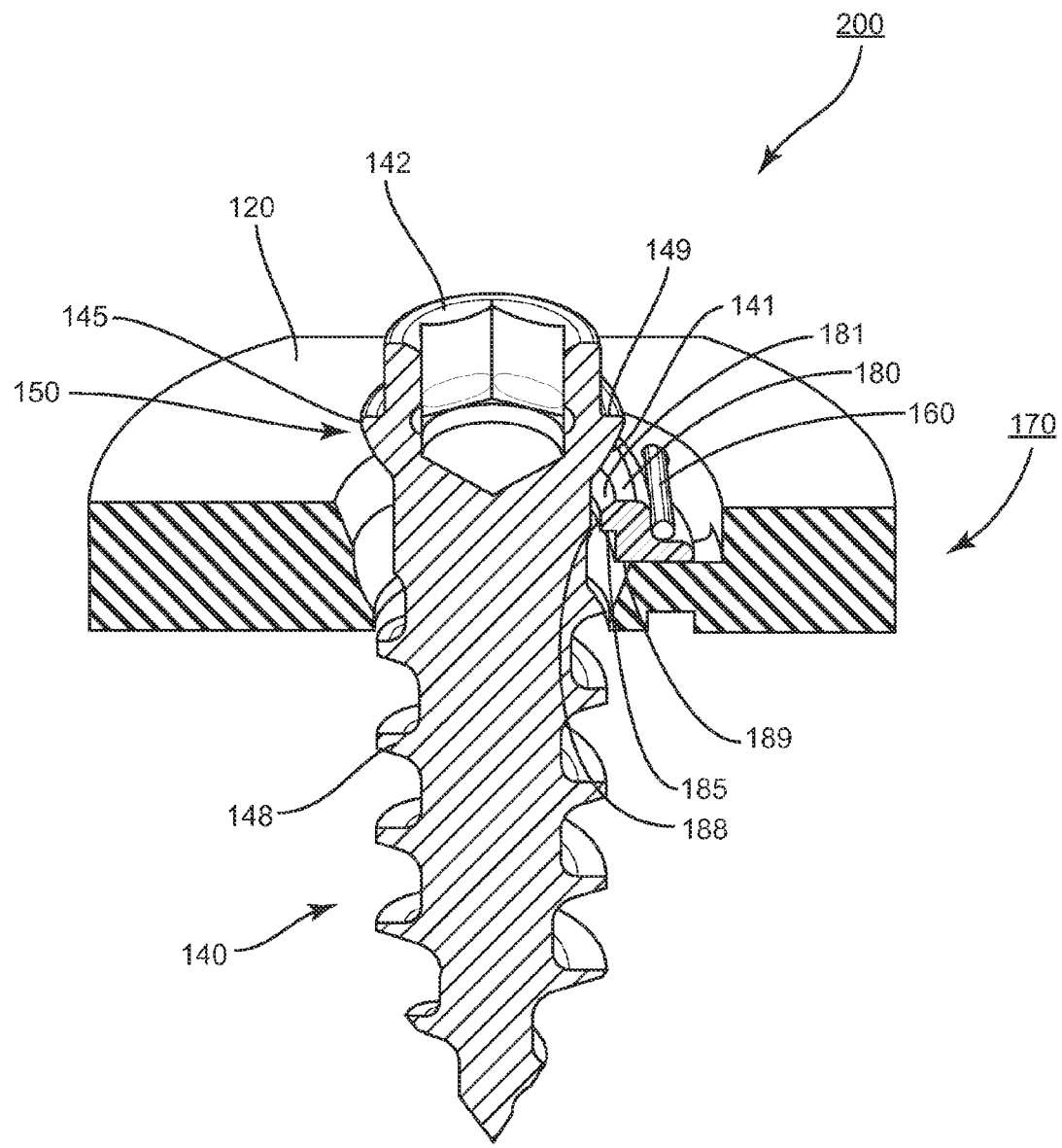
FIG. 17 is a cross-sectional, top-isometric view of the system of FIG. 5.

FIG. 17 shows a cross-sectional, top-isometric view of the system 200 of FIG. 16. As shown in FIG. 17, the fastener 140 further comprises a ridge line 145 of ledge 150 that is situated the intersection of the upper surface 149 and the underside surface 141 of ledge 150. Further, as shown in FIG. 17, the shoulder element 180 comprises an interior surface 188 situated between the lip 181 and the first underside surface 185. As shown in FIG. 17 in combination with FIG. 10, the groove areas 183 is defined by the areas adjacent each of the first underside surface 185 and the second underside surface 189 of the shoulder element 180, as well as that adjacent the surface between the first underside surface 185 and the second underside surface 189. Thus, the groove areas 183 accommodate the ledge 150 of fastener 140.

Figure 18:
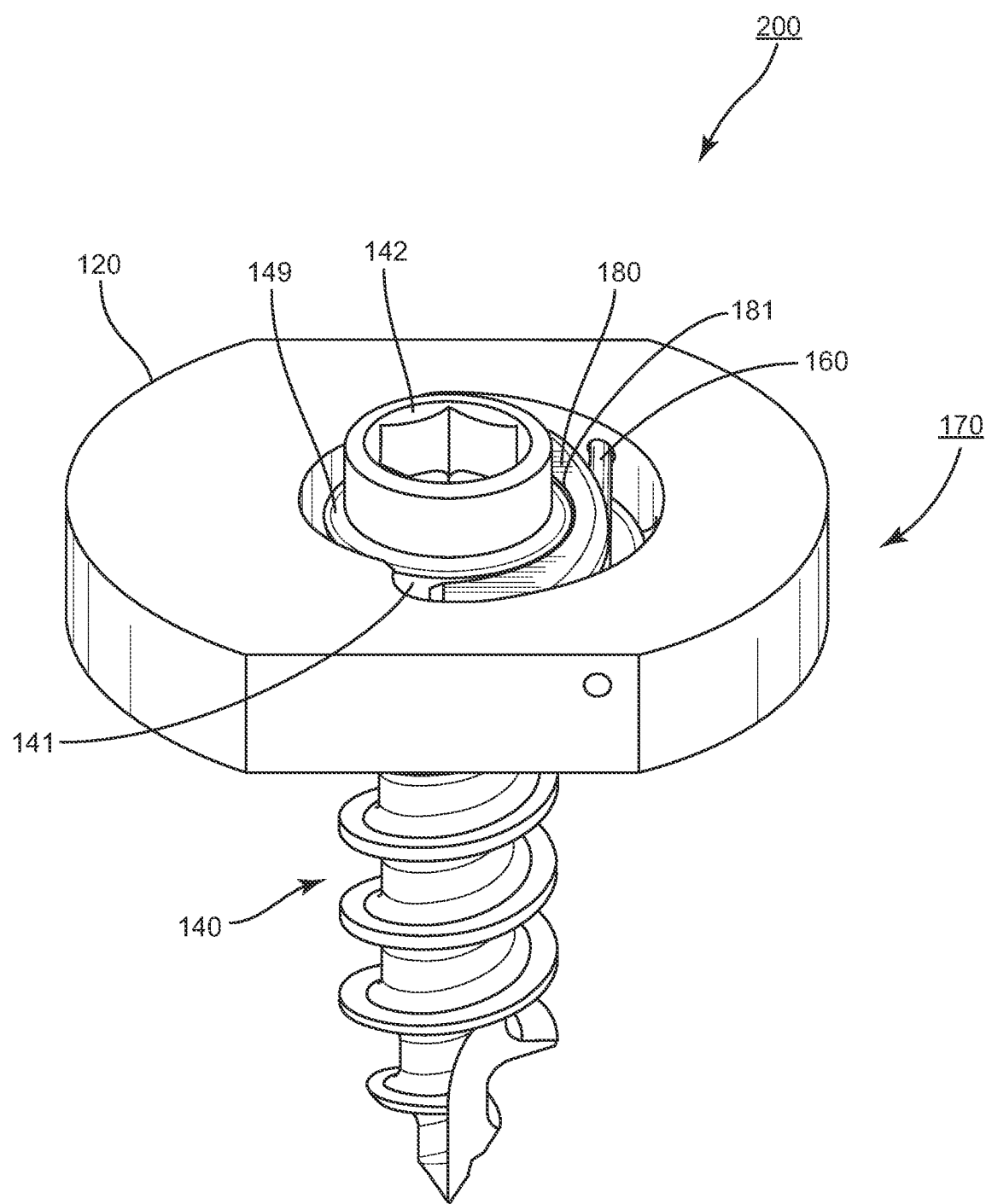
FIG. 18 is a top, isometric view of the system of FIG. 5.

FIG. 18 shows a top, isometric view of system 200 which comprises retaining mechanism 170 and a fastener 140. As shown in FIG. 18, the shoulder element 180 and the retaining element 160 have both been placed into the stratum 120, but as compared to that shown in FIGS. 16 and 17, the fastener 140 has been partially inserted into the hole 122 to the point where the ridge line 145 of ledge 150 of fastener 140 contacts the interior surface 188 of the shoulder element 180. Further, as shown in FIG. 18, at this point of insertion of the fastener 140, the shoulder element 180 is in its first position that allows insertion of the fastener 140 into the at least one hole 122. Specifically, as shown in FIG. 18, at this point, the fastener 140 is imparting a force against the shoulder element 180 which moves the shoulder element 180 radially outward and toward the retaining element 160, which itself deflects slightly, allowing the shoulder element 180 to move from its second position into its first position.

Figure 19:
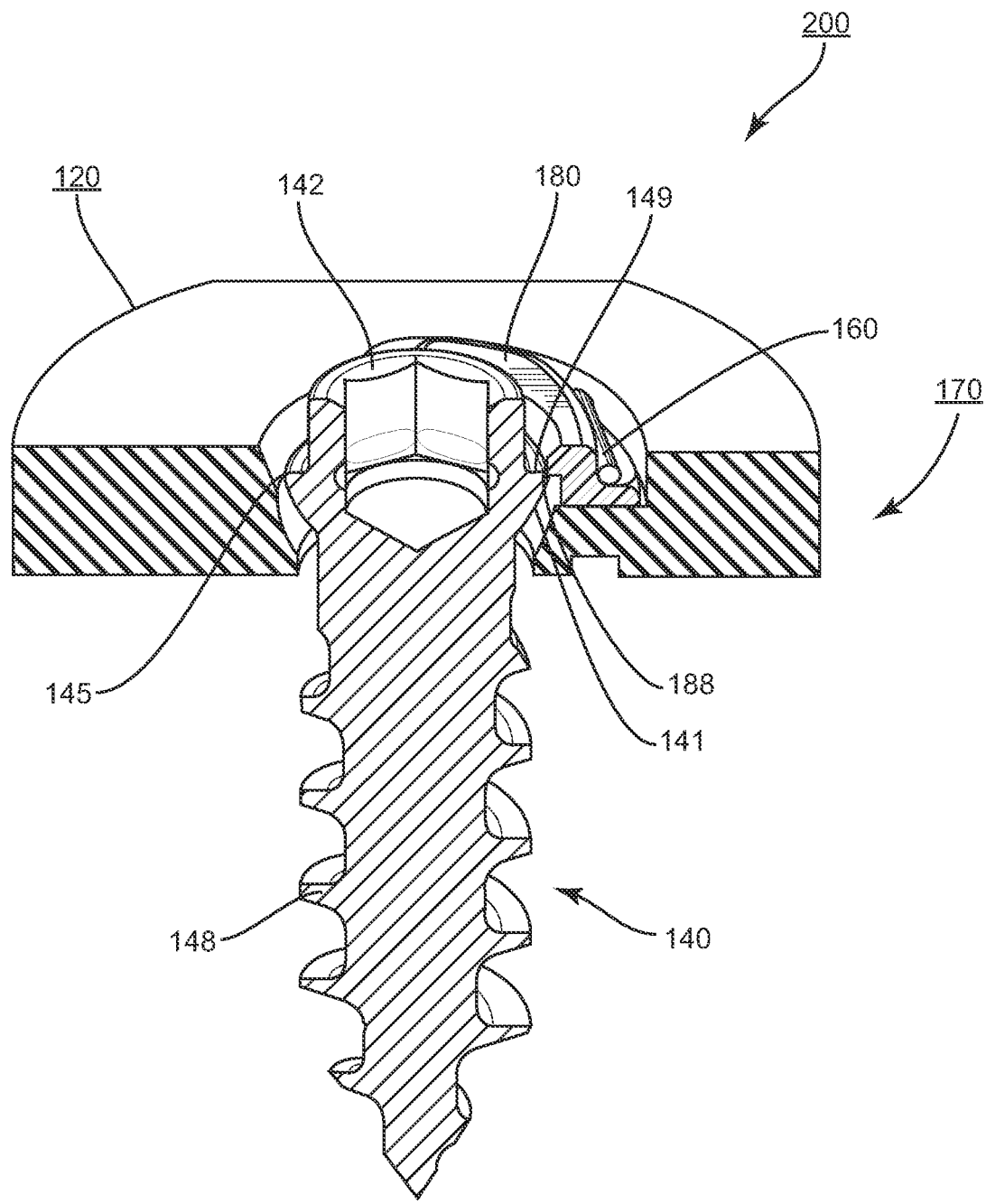
FIG. 19 is a cross-sectional, top-isometric view of the system of FIG. 5.

FIG. 19 shows a cross-sectional, top-isometric view of the system 200 of FIG. 18. As shown in FIG. 19, the ridge line 145 of ledge 150 of fastener 140 contacts the interior surface 188 of the shoulder element 180. Thus, the fastener 140 is imparting a force against the shoulder element 180 which moves the shoulder element 180 radially outward and toward the retaining element 160. The retaining element 160 deflects slightly, allowing the shoulder element 180 to move from its second position into its first position.

Figure 20:
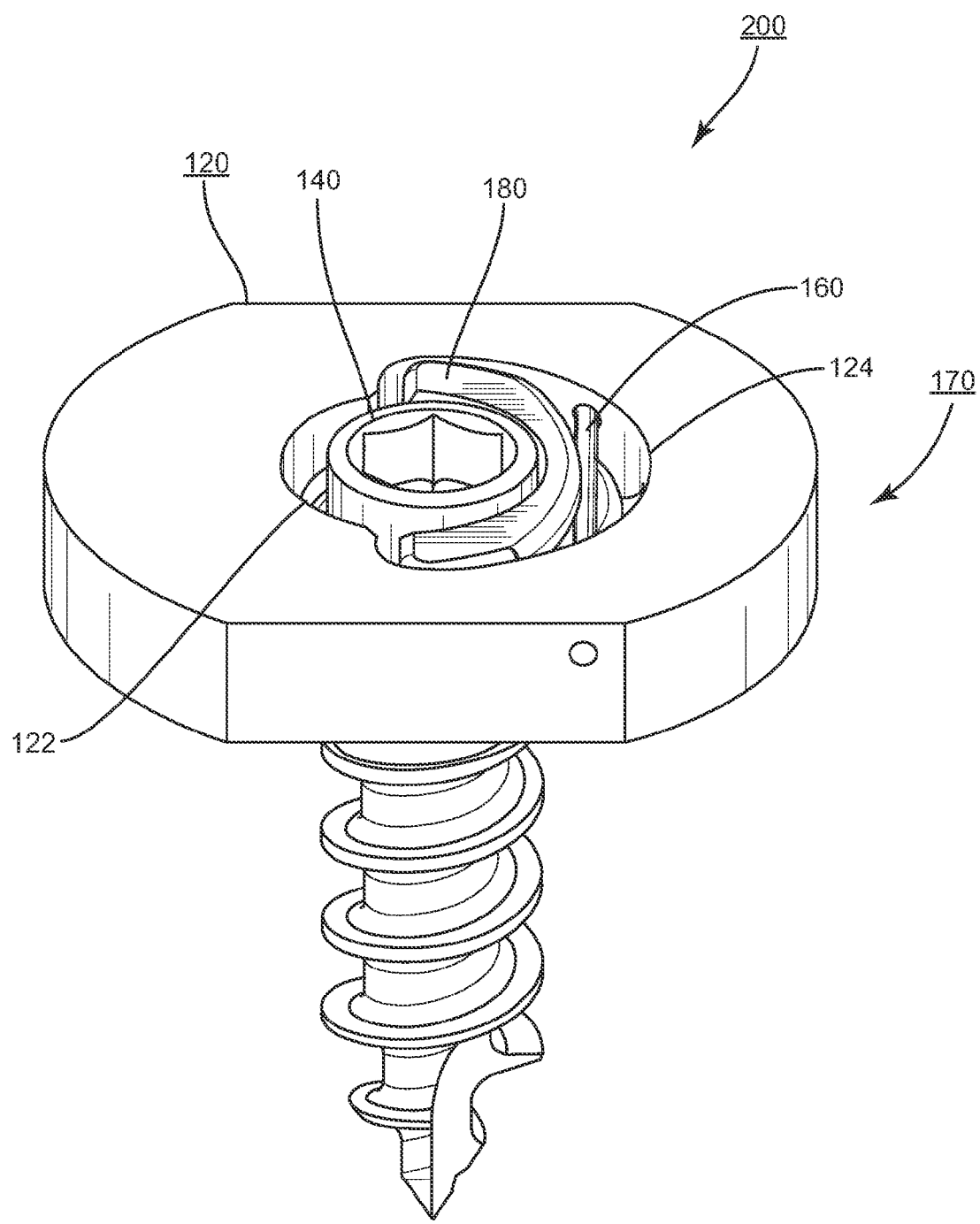
FIG. 20 is a top, isometric view of the system of FIG. 5.

FIG. 20 shows a top, isometric view of system 200 which comprises retaining mechanism 170 and a fastener 140. As shown in FIG. 20, the shoulder element 180 and the retaining element 160 have both been placed into the stratum 120, and the fastener 140 has been fully inserted into the hole 122. At this point, after the fastener 140 is in its fully-inserted position, the retaining element 160 is configured to engage the stratum 120 and configured to at least partially overlap the shoulder element 180 such that the shoulder element 180 helps prevent inadvertent backing out of the fastener 140.

Figure 21:
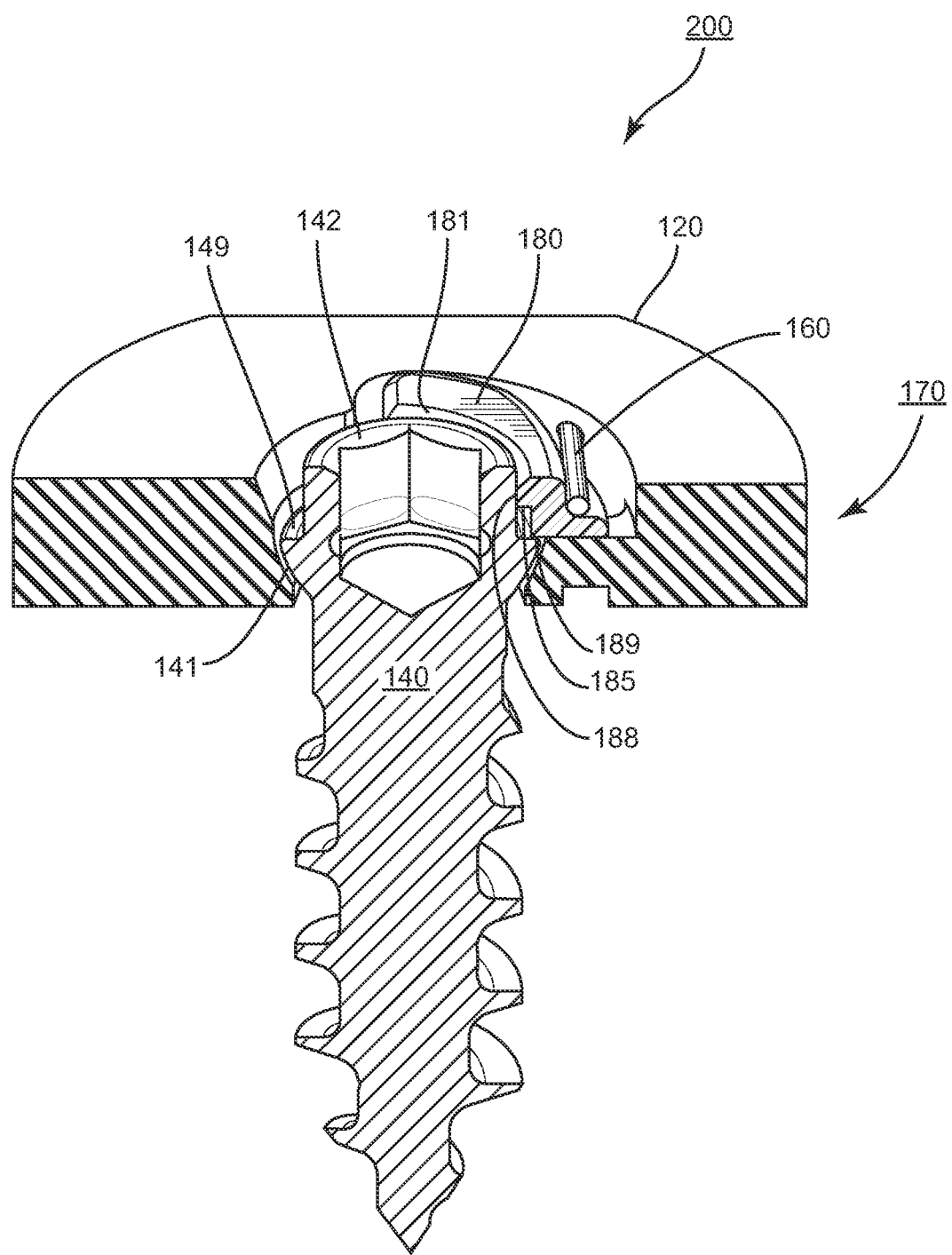
FIG. 21 is a cross-sectional, top-isometric view of the system of FIG. 5.

FIG. 21 shows a cross-sectional, top-isometric view of the system 200 of FIG. 20. As shown in FIG. 21, the shoulder element 180 is in its second position. As compared to FIGS. 18 and 19, when the fastener 140 has moved farther into the hole 122, the ridge line 145 of ledge 150 of fastener 140 has passed the interior surface 188 of the shoulder element 180. Thus, after the fastener 140 is in its fully-inserted position, as shown in FIG. 21, the retaining element 160 engages the stratum 120 and at least partially overlaps the shoulder element 180 such that the shoulder element 180 helps prevent inadvertent backing out of a fastener 140. Specifically, the retaining element 160 imparts a force against the shoulder element 180 in a direction toward fastener 140, and thereby, locking the shoulder element 180 in place engaged with the stratum 120, and thereby, helping to maintain pressure on the fastener 140. In this manner, the second underside surface 189 of the shoulder element 180 imparts a force against the upper surface 149 of ledge 150 of the head 142 of the fastener 140, thereby preventing inadvertent backing out of the fastener 140, i.e., backing out from hole 122. Accordingly, the ledge 150 of the head 142 of fastener 140 is configured such that upon insertion of the fastener 140 in the at least one hole 122, the ledge 150 will engage the lip 181 on the shoulder element 180, thereby placing the shoulder element 180 into the first position, and such that when the fastener 140 is in its fully-inserted position, the shoulder element 180 is in its second position.

As shown in FIG. 21, the fastener 140 enters the hole 122 at an angle relatively perpendicular to the stratum 120. Note that in certain circumstances, it may be desired that the fastener 140 enter the hole 122 of the stratum 120 at an angle that is not perpendicular or, at least, less so than that shown in FIG. 21. For example, as shown in FIG. 4, fastener 40 has been inserted into stratum 20 at an angle of approximately 20 degrees from perpendicular. In such example, as shown in FIG. 4, the first underside surface 85 of the shoulder element 80 may be used to impart a force against the upper surface 49 of the ledge of the fastener 40, thereby preventing inadvertent backing out of the fastener 40, i.e., backing out from hole 22.

As shown in the Figures and as described herein, the bone may be, for example, part of a spine such as a vertebral body or vertebral bodies, the stratum 20 may be, for example, a spinal plate, and the fastener 40 or 140 may be, for example, a screw.

In the embodiments described herein, the stratum 20 and/or 120 may be made of a variety of biocompatible materials (metal or non-metal), including but not limited to, Titanium Alloys, commercially available Titanium, stainless steel, polyetheretherketone ("PEEK"), cobalt chrome ("CoCr"), polyetherketoneketone ("PEKK"), ultra high molecular weight polyethylene ("UHMWPE"), polyethylene, shape memory metals, other polymers or any combination of such materials. Similarly, the shoulder element 80 and/or 180 and/or the fasteners 40, 40A or 140 may be made of the same materials. Also, any suitable materials know in the art may work for each of these elements. Further, in the embodiments described herein, the shoulder element 80 and/or 180 is substantially rigid.

The term "substantially" as used herein may be applied to modify any quantitative representation which could permissibly vary without resulting in a change in the basic function to which it is related. For example, a shoulder element 80 or 180 may be considered substantially rigid if when the fastener 40, 40A or 140 is in its fully-inserted position and the shoulder element 80 or 180 at least partially overlaps a hole, for example, hole 22, 22A or 122, the shoulder element 80 or 180 does not deflect enough to allow the fastener, for example, 40, 40A or 140, to inadvertently back out of the stratum 20 or 120.

All adjustments and alternatives described above are intended to be included within the scope of the invention, as defined exclusively in the following claims. Those skilled in the art also should realize that such modifications and equivalent constructions or methods do not depart from the spirit and scope of the present disclosure, and that they may make various changes, substitutions, and alterations herein without departing from the spirit and scope of the present disclosure. Furthermore, as used herein, the terms components and modules may be interchanged. It is understood that all spatial references, such as "superior," "inferior," "anterior," "posterior," "outer," "inner," "upper," "underside," "top," "bottom," and "perimeter" are for illustrative purposes only and can be varied within the scope of the disclosure.

The invention claimed is:

1. A system for affixing a stratum to bone comprising:
a stratum defining a plate comprising a first surface, a second surface, and a hole extending between the first surface and the second surface, wherein the second surface is configured to engage at least a portion of the bone, and a shoulder element is slidably disposed in a recess of the stratum adjacent to the hole; and
a retaining element,
wherein the shoulder element is configured to slide with respect to the stratum between the first position and the second position upon insertion of the fastener into the hole, the shoulder element slides to the first position as the fastener engages the shoulder element causing the shoulder element to slide with respect to the stratum and, a force exerted on the shoulder element by the retaining element causes the shoulder element to slide with respect to the stratum to a second position after the fastener is inserted into the hole.

2. The system of claim 1, wherein the stratum is configured to engage the retaining element.

3. The system of claim 1, wherein the shoulder element is C-shaped.

4. The system of claim 1, wherein the shoulder element is substantially rigid.

5. The system of claim 1, wherein:
the bone is spine, and the stratum is a spinal plate.

6. The system of claim 1, further comprising:
a fastener configured to pass through the hole and engaging the bone.

7. The system of claim 1, wherein the retaining element is rod-shaped.

8. The system of claim 1, wherein the retaining element comprises material having elastic properties.

9. The system of claim 1, wherein the retaining element comprises Nickel Titanium or other Titanium alloy.

10. A system for affixing a stratum to bone, the system comprising:
a stratum defining a plate having a first surface, a second surface, and a hole extending between the first surface and the second surface, wherein the second surface is configured to engage at least a portion of the bone;
a shoulder element slidably disposed in a recess of the stratum adjacent the hole;
a fastener configured to pass at least partially through the hole and configured to engage the at least a portion of the bone, the fastener further comprising:
a head portion configured for manipulation by a user; and
a shaft portion configured to engage at least a portion of the bone; and
a retaining element,
wherein the shoulder element is configured to slide with respect to the stratum between the first position and the second position upon insertion of the fastener into the hole, the shoulder element slides to the first position as the fastener engages the shoulder element causing the shoulder element to slide with respect to the stratum and, a force exerted on the shoulder element by the retaining element causes the shoulder element to slide with respect to the stratum to a second position after the fastener is inserted into the hole.

11. The system of claim 10, wherein the stratum further comprises:
a second hole between the first surface and the second surface;
a second shoulder element slidably engaged to a portion of the stratum, adjacent the second hole and configured to at least partially overlap the second hole;
a second fastener configured to pass at least partially through the second hole and configured to engage the at least a portion of the bone; and
a second retaining element configured to engage the stratum and configured to at least partially overlap the second shoulder element such that the second shoulder element helps prevent inadvertent backing out of the second fastener after the second fastener has been fully inserted into the second hole.

12. The system of claim 10, wherein the shoulder element is C-shaped.

13. The system of claim 10, wherein the shoulder element is substantially rigid.

14. The system of claim 10, wherein the retaining element is rod-shaped.

15. The system of claim 10, wherein the retaining element comprises material having elastic properties.

16. The system of claim 10, wherein the retaining element comprises Nickel Titanium or other Titanium alloy.

17. A system for affixing a stratum to bone, the mechanism comprising:
a stratum defining a plate comprising a first surface, a second surface, and a hole extending between the first surface and the second surface, wherein the second surface is configured to engage at least a portion of the bone, and a shoulder element slidably engaged to a portion of the stratum configured to at least partially overlap the hole, the shoulder element comprising:
a first position that allows insertion of a fastener into the hole; and
a second position that at least partially overlaps the hole; and
a retaining element configured to engage the stratum and configured to at least partially overlap the shoulder element such that the shoulder element helps prevent inadvertent backing out of a fastener after the fastener has been fully inserted into the hole;

wherein the shoulder element is configured to slide with respect to the stratum between the first position and the second position upon insertion of the fastener into the hole, the shoulder element slides to the first position as the fastener engages the shoulder element causing the shoulder element to slide with respect to the stratum and, a force exerted on the shoulder element by the retaining element causes the shoulder element to slide with respect to the stratum to a second position after the fastener is inserted into the hole.

18. The system of claim 17, further comprising:

a fastener configured to pass through the hole in the stratum and engaging the bone, wherein the fastener comprises a head and a shaft, the head configured for manipulation by a user and a shaft configured to engage at least a portion of bone, the head comprising a ledge configured such that upon insertion of the fastener in the hole, the ledge will engage a lip on the shoulder element, thereby placing the shoulder element into the first position, and such that when the fastener is in its fully inserted position, the shoulder element is in its second position.

* * * * *